United States Patent [19]

Gras

[11] Patent Number: 4,925,974

[45] Date of Patent: May 15, 1990

[54] PROCESS FOR PRODUCING BLOCKED, UREA GROUP-CONTAINING POLYISOCYANATES

[75] Inventor: Rainer Gras, Bochum, Fed. Rep. of Germany

[73] Assignee: Huels Aktiengesellschaft, Marl, Fed. Rep. of Germany

[21] Appl. No.: 245,217

[22] Filed: Sep. 16, 1988

[30] Foreign Application Priority Data

Nov. 21, 1987 [DE] Fed. Rep. of Germany ....... 3739480

[51] Int. Cl.$^5$ ............... C07C 119/042; C07C 119/045; C07C 119/048; C07D 211/56
[52] U.S. Cl. .................................. 560/336; 560/351; 546/244; 564/1.5
[58] Field of Search .............................. 560/336, 351; 260/96.5 R; 546/244

[56] References Cited

U.S. PATENT DOCUMENTS

| | | | |
|---|---|---|---|
| 3,392,183 | 7/1968 | Windemuth et al. | 560/336 |
| 3,926,875 | 5/1987 | Tsugukuni et al. | 560/336 |
| 4,410,678 | 9/1988 | Holubka et al. | 560/336 |

FOREIGN PATENT DOCUMENTS

| | | | |
|---|---|---|---|
| 2020905 | 2/1971 | Fed. Rep. of Germany | 560/336 |
| 3143060 | 5/1983 | Fed. Rep. of Germany | 560/336 |
| 1233866 | 4/1975 | France | 560/336 |

*Primary Examiner*—Mary C. Lee
*Assistant Examiner*—Robert C. Whittenbaugh
*Attorney, Agent, or Firm*—Oblon, Spivak, McClelland, Maier & Neustadt

[57] ABSTRACT

A process for the production of a blocked urea group-containing polyisocyanate from a partially blocked polyisocyanate and polyamine, comprising the steps of:
 (i) reacting a partially blocked polyisocyanate, said polyisocyanate being made substantially free of monomeric polyisocyanate, by vacuum thin layer evaporation with a primary polyamine, secondary polyamine, or mixtures thereof, in relative proportions such that the ratio of isocyanate groups to amino groups is in the range from about 1:1 to 1.3:1, and
 (ii) isolating said urea group-containing polyisocyanate by wherein the vacuum boiling point of said polyisocyanate is lower than the deblocking temperature of said urea group-containing polyisocyanate.

20 Claims, No Drawings

PROCESS FOR PRODUCING BLOCKED, UREA GROUP-CONTAINING POLYISOCYANATES

BACKGROUND OF THE INVENTION

1. Field of the Invention

The invention relates to a process for manufacturing blocked, urea group-containing polyisocyanates from semi-blocked polyisocyanates and polyamines.

2. Discussion of Background

The reaction of polyisocyanates with polyamines is so violent that "it has priority over all other isocyanate reactions" (cf. Houben-Weyl, Methoden der Organischen Chemie. Vol. XIII, p. 132). This high reactivity may also be the reason for the fact that for a long time little research has been done on the direct reaction between polyamines and polyisocyanates to the corresponding urea derivatives.

Of course, in principle symmetrical urea derivatives can be obtained through direct conversion of polyisocyanates and water according to the process designated in DE-OS No. 23 41 065, but with this process one must accept the fact that gaseous reaction products, which must be carefully removed, are produced during the formation of urea. Furthermore, the reaction between water and isocyanate has the drawback that there is limited variability and in using the stoichiometric method, oligomeric urea will form, leaving monomeric polyisocyanate. In addition to this, DE-OS No. 23 41 065 teaches that frequently an excess of polyisocyanate-isophorone-diisocyanate is added or that due to viscosity reasons, solvents must be used.

Another disadvantage is that the high reactivity of the reaction between a polyamine and polyisocyanate results in a reaction that can be controlled only with difficulty, and results in a wide range of molecular weights.

This reaction is also observed in the preparation of biuret polyisocyanates and represents there an undesired secondary reaction (cf. DE-OS No. 22 61 065, OS No. 26 09 995 and U.S. Pat. No. 3,903,126).

Finally, in the DE-OS No. 31 43 060 a process for preparing blocked, urea group-containing isophoronediisocyanate adducts is described. Such compounds are obtained by converting 3-isocyanatomethyl-3,5,5-trimethylcyclohexylisocyanate, also called isophorone diisocyanate (IPDI), that are partially blocked with epsilon-caprolactam, and diamines having two sterically feasible primary and/or secondary amino nitrogens. The reaction is performed neat and, for viscosity reasons, must occur above 130° C. and, as demonstrated in the examples, even at 160° C. If the partial blocking of IPDI is carried out according to the directives in DE-OS No. 31 43 060, then as the reaction equation shows and it would be desirable,

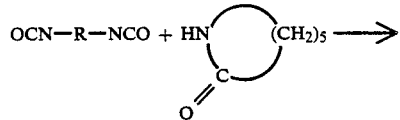

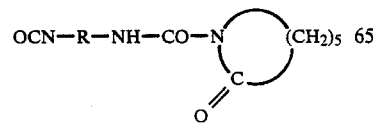

-continued

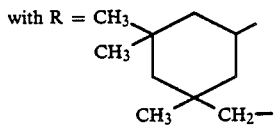

not only the partially-blocked IPDI adduct but also completely blocked IPDI is obtained while retaining from 15 to 17% by weight non-reacted, thus unblocked monomeric IPDI. This high monomer content has a very grave disadvantage, since during the reaction with diamines, it is responsible for the formation of undesired polymeric urea compounds.

According to DE-OS No. 31 43 60, further reactions of the partially blocked polyisocyanates with polyamines are unsuitable for producing urea compounds that are interesting for polyurethane chemistry.

SUMMARY OF THE INVENTION

Therefore, one object of the present invention is a process for producing blocked urea group-containing polyisocyanates from partially-blocked polyisocyanates and polyamines.

This and other objects which will become apparent from the following specification have been achieved by the process for the production of blocked urea group-containing polyisocyanates from a partially blocked polyisocyanate and a polyamine, comprising the steps of:

(i) reacting a partially blocked polyisocyanate, said polyisocyanate being made substantially free of monomeric polyisocyanate, by vacuum thin layers evaporation with a primary polyamine, secondary polyamine, or mixtures thereof, in relative proportions such that the ratio of isocyanate groups to amino groups is in the range from about 1:1 to 1.3:1, and (ii) isolating said urea group-containing polyisocyanate by wherein the vacuum boiling point of said polyisocyanate is lower than the deblocking temperature of said urea group-containing polyisocyanate.

DETAILED DESCRIPTION OF THE PREFERRED EMBODIMENTS

Formulas I and II illustrate the type of polyamines that may be used in the present process:

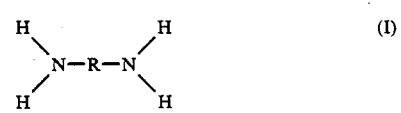

in which R is —(CH$_2$)—$_{2-36}$, or C$_{2-36}$ branched alkyl,

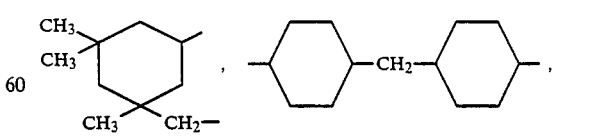

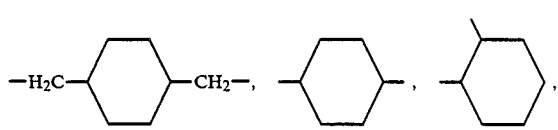

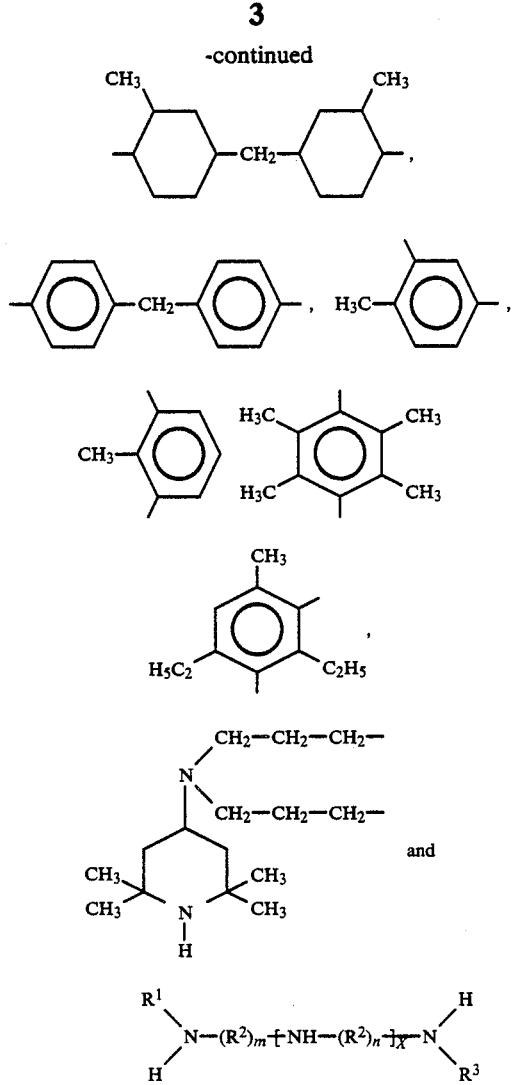

$$\begin{array}{c} R^1 \\ \diagdown \\ N-(R^2)_m-[NH-(R^2)_n-]_X-N \\ \diagup \\ H \end{array} \begin{array}{c} H \\ \diagdown \\ \diagup \\ R^3 \end{array} \quad (II)$$

in which $R^1$ is the same as or different from $R^3=H$, straight chain or branched alkyl, cycloalkyl-, aryl-, aralkyl, $R^2$ is —CH$_2$— or if desired, a branched alkyl group, in which the polyamine contains from 2 to 36 carbon atoms, and m=2 to 8, X=0 to 6, and n=2 to 8.

The polyisocyanates to be added according to the invention are described for example in "Methoden der Organischen Chemie," Houben-Weyl, Vol. 14/2, 4th edition, Georg Thieme Verlag Stuttgart, 1963, pp. 61–70 and in W. Siefken, Liebigs Ann. Chem. 562, pp. 75–136.

By using a partially blocked polyisocyanate containing 6.5% by weight of monomeric polyisocyanate, preferably up to 3.5% by weight and in particular up to 2.5% by weight, it is possible to obtain an additional reaction. These partially blocked polyisocyanates may be produced by reacting a large excess of polyisocyanate (5 to 20 mole) with the blocking agent (1 mole) at temperatures ranging from 50° C. to 130° C., preferably from 70° C. to 100° C., and subsequently separating the excess polyisocyanate by means of conventional thin-layer evaporation. This process is disclosed in U.S. application Ser. No. 07/243,605, filed Sept. 13, 1988 incorporated herein by reference.

Only those polyisocyanates whose boiling points under vacuum are below the deblocking temperature of the blocking agent added are suitable and thus those which can be separated by means of thin-layer evaporation.

Particularly preferred aliphatic, (cyclo)aliphatic and aromatic polyisocyanates are those which are technically readily accessible such as 1,6-hexamethylene diisocyanate (HDI), 2,2,4(2,4,4)-trimethylhexamethylene diisocyanate (TMDI), 2-methylpentane-1,5-diisocyanate (DI51), and 2,4- or 2,6-toluylene diisocyanate, and in particular 3-isocyanatomethyl-3,5,5-trimethylcyclohexylisocyanate (IPDI) and their mixtures of isomers.

For manufacturing polyisocyanate-urea-adducts according to the invention, polyamines having primary and/or secondary amino groups are suitable. They preferably have from 2 to 36 carbon atoms and can be aliphatic or have one or more cycloaliphatic, aromatic or heterocyclic rings having from 5 to 8 substituents. The polyamines that can be added can also carry tertiary amino groups. Non-limiting examples of suitable polyamines include:

(i) non-branched primary alkylene diamines, such as ethylene diamine, trimethylene diamine, tetramethylene diamine, hexamethylene diamine, octamethylene diamine, dodecamethylene diamine and the C$_{36}$-diamine, (ii) branched primary alkylene diamines, such as 2-methyl-pentamethylene diamine, 2,2,4(2,4,4)-trimethylhexamethylene diamine and 5-methylnonamethylene diamine, (iii) cycloaliphatic primary diamines such as 1,4(1,2)-diaminocyclohexane, 2,4(2,6)-diamino-1-methylcyclohexane, 4,4'-diaminodicyclohexylmethane, 4,4'-diamino-3,3'-dimethyldicyclohexylmethane, and 4,4'-diamino-3,3'5,5'-tetramethyldicyclohexylmethane, (iv) cycloaliphatic/aliphatic primary or secondary diamines, such as N-cyclohexyl-1,3-propylene diamine, bis-(1,4-aminomethyl)-cyclohexane and 3-aminomethyl-3,5,5-trimethylcyclohexylamine (isophorone diamine IPD), (v) aliphatic primary and secondary polyamines such as diethylene triamine, triethylene tetramine, tetraethylene pentamine, pentaethylene hexamine, dipropylene triamine, dihexamethylene triamine, dioctamethylene triamine, and bis-(3-aminopropyl)ethylene diamine, (vi) aromatic primary diamines such as 3,5-diethyltoluylene diamine, 2,4(2,6)-toluylene diamine, 1,4-diamino-2,3,5,6-tetramethylbenzene and 4,4-diaminodiphenylmethane, (vii) aliphatic secondary diamines such as 1,1,6,6-tetraisopropyl-2,5-diazahexane and N,N'-diisobutyl isophorone diamine, (viii) heterocyclic diamines such as 4-(3-aminopropyl-amino)- 2,2,6,6-tetramethylpiperidine and 4[(bis-3-aminopropyl)amino]-2,2,6,6-tetramethylpiperidine, (ix) and their mixtures.

Melamine and water may also be used.

The addition of the aforementioned heterocyclic compounds is of a great interest since the manufacture of permanent ultraviolet-stable plastics, and in particular paint systems, are then feasible. In this method they function not only as an additive but rather they are incorporated directly into the macromolecule.

According to the invention, suitable blocking agents are those which deblock at curing conditions, i.e. between 140° and 220° C. This includes alcohols, e.g. methanol, ethanol, ispropanol, cyclohexanol; oximes such as acetone oxime, methylisobutyl ketoxime; mercaptans; lactams, for example lauryl lactam, acetoacetic ester, malonic ester, and especially epsilon-caprolactam and methyl ethyl ketoxime (cf. "Methoden der Organischen Chemie," Houben-Weyl, Vol. 14/2, 4th edition, Georg Thieme Verlag Stuttgart, 1963, p. 61 ff.).

In the process of the invention, the curing agent is manufactured in the solvent and in particular such that the partially blocked polyisocyanate is present in the solvent and the polyamine is added dropwise either neat or also dissolved in a solvent. Suitable solvents are, on the one hand, those that can be readily removed such as toluene, xylene, cyclohexane, special benzene with less than 1% by vol. of aromatics (a mixture of mainly aliphatic, cycloaliphatic and aromatic hydrocarbons with a boiling point between 60°-96° C.), acetic ester and acetone, in order to isolate the polyisocyanate-urea-adducts of the invention; on the other hand, such solvents as toluene, xylene, SOLVESSO® 100 and 150 (mixture of aromatics produced by Esso), tetraline, cumene, methylisobutyl- and diisobutyl ketone, hexyl acetate, butyl acetate, ethylene glycol diacetate (EGA), methoxypropyl acetate (MOP-acetate), butylene glycol diacetate etc., which in industry are added for solvent-containing paint systems.

The aforementioned compounds can also be used as mixtures. The concentrations of polyisocyanate-urea-adducts can vary widely. Concentrations ranging from 30 to 70% by weight have proven to be advantageous.

According to the invention, the reaction takes place between room temperature and 80° C., preferably between room temperature and 70° C. Following successful addition of polyamine it is preferable to heat the reaction mixture to, if desired, a temperature ranging from 100° to 120° C. If the reaction product is to be liberated from the solvent, this can be done by simply applying a vacuum. Melt extrusion in an evaporation screw is especially suitable for removing the solvent.

The use of special benzenes having less than 1% by vol. of aromatics or cyclohexane as solvent has proven to be an especially advantageous process for manufacturing permanent, blocked polyisocyanate-urea-adducts according to the invention. In this process the reaction is carried out at room temperature, and in particular such that the partially-blocked polyisocyanate is dissolved in special benzene or cyclohexane and with intensive stirring, the polyamine is added dropwise in such a manner that the reaction temperature does not exceed 70° C. The reaction product precipitates out during the dropwise addition. Following completion of the amine addition, stirring is continued from 30 to 45 minutes and the solvent is subsequently removed.

In the conversion process of the invention, the reaction partners—polyisocyanate and polyamine—are added in such proportions as to give a ratio of isocyanate groups to amino groups of 1-1.3:1, preferably one isocyanate group per primary and/or secondary amino group. In general, the adducts of the invention have an NCO content ranging from 4 to 20%, preferably from 6 to 15% by weight. The free isocyanate content ranges from about 0.7% by weight to 5% by weight. The polyisocyanate addition products have a melting range from 90° to 210° C. They are especially suitable as curing agents for highly functional compounds having Zerewitinoff active hydrogen atoms. Combined with such compounds having Zerewitinoff active hydrogen atoms, above 140° C., preferably from 180° to 220° C., the polyaddition products result in systems that cure to high-grade plastics. Probably the most important application area for such systems is their use as linkers for PUR powder paint and solvent-containing single component-PUR-varnish.

The compounds of the invention are suitable as intermediate products for manufacturing plastics, in particular paints. Therefore, they are especially valuable because they also facilitate, in a simple manner, the manufacture of PUR varnish having a reduced degree of gloss.

Other features of the invention will become apparent according to the following descriptions of the exemplary embodiments which are given for illustration of the invention and are not intended to be limiting thereof.

EXAMPLES

Example 1

A. Preparation of partially blocked polyisocyanates
General preparation

One mole of blocking agent was added in proportions of from 5 to 20 moles of polyisocyanate at temperatures ranging from 70° to 80° C. with stirring. After the completed addition of the blocking agent, the reaction mixture was then heated at 100° C. for another hour and subsequently the non-reacted polyisocyanate was removed via thin-layer evaporation at temperatures ranging from 90° to 140° C. and at 0.0133 mbar. The chemical and physical characteristic values of the reaction product (=residue) were determined and compiled in the following table.

| | Starting Materials | | Partially blocked polyisocyanates | | | | | | | |
|---|---|---|---|---|---|---|---|---|---|---|
| | | | NCO content in % by weight | | Polyisocyanate monomer | Viscosity in mPa's | | | | |
| Examples A | polyiso-cyanate | blocking agent | free | total | % by wt. | 25° C. | 30° C. | 40° C. | 50° C. | 70° C. |
| 1 | IPDI | caprolactam | 12.4 | 24.8 | <1.0 | 1250000 | 410000 | 63500 | 13700 | 1250 |
| 2 | IPDI | caprolactam | 11.5 | 24.5 | 2.2 | 1145000 | 397000 | 61250 | 12530 | 1070 |
| 3 | IPDI | caprolactam | 11.6 | 24.4 | 3.5 | 1120000 | 360000 | 59500 | 11500 | 980 |
| 4 | IPDI | caprolactam | 11.8 | 24.5 | 4.6 | 660000 | 194000 | 34000 | 8550 | 680 |
| 5 | IPDI | caprolactam | 11.85 | 24.6 | 6.4 | 451000 | 101000 | 22000 | 4500 | 450 |
| 6 | IPDI | MEK-oxime | 12.8 | 26.5 | 2.8 | 571000 | 152000 | 27500 | 5500 | 420 |
| 7 | HDI | caprolactam | 15.3 | 29.4 | 0.5 | 100 | 80 | 50 | 30 | <30 |
| 8 | HDI | MEK-oxime | 15.8 | 32.4 | 2.5 | 70 | 60 | 50 | 30 | <30 |
| 9 | DI51 | caprolactam | 14.8 | 29.3 | 0.7 | 160 | 120 | 60 | 45 | <30 |
| 10 | DI51 | MEK-oxime | 15.7 | 31.5 | 0.8 | 190 | 150 | 80 | 60 | 30 |
| 11 | DI51 | MEK-oxime | 16.5 | 32.9 | 7.5 | 110 | 70 | 40 | <30 | <30 |

B. Preparation of blocked polyisocyanate-urea-adducts according to the invention With respect to the free NCO content, the equivalent quantities of a 50 to 70% solution in toulene of a diamine or polyamine or their mixtures were added in such a manner to a 50 to 70% solution in toluene of a partially blocked polyisocyanate, with intensive stirring, at a temperature ranging from 55° to 65° C. such that the reaction temperature does not exceed 70° C. Following completion of amine addition, the reaction mixture was then heated for a period ranging from 30 to 45 minutes. During this time, the temperature was slowly increased to from 100° to 120° C. Then the toluene was removed from the reaction product under vacuum at 0.133 mbar. The following table lists the chemical and physical characteristics of the reaction products.

(a) IPDI-urea-adducts according to A 2 and amine component (b) IPDI-urea-adducts according to A 1 and amine component (c) HDI-urea-adduct according to A 7 and amine component (d) DI51-urea-adducts according to A 9 and amine component (e) IPDI-urea-adducts according to A 3, A 4, A 5 and amine component (f) IPDI-urea-adducts according to A 2 in such proportions as to give a ratio of NCO to $NH_2$ ranging from 1.05 to 1.3:1 and amine component (g) IPDI-urea-adducts according to A 2 and amine component, prepared at a temperature ranging from 40° and 110° C.

(h) IPDI-urea-adducts according to A 2 and amine component, prepared in acetone or acetic ester (i) IPDI-urea-adducts according to A 2 and water (j) IPDI-urea-adducts according to A 2 and amine component, prepared in special benzene and cyclohexane

|   | amine component | NCO content (% by weight) latent | Free | melting range °C. | glass transition temperature (DTA) °C. |
|---|---|---|---|---|---|
| Example B a | | | | | |
| 1 | 1,6-hexamethylene diamine | 10.8 | 0.15 | 120–122 | 51–66 |
| 2 | 1,8-octamethylene diamine | 10.5 | 0.5 | 101–103 | 41–61 |
| 3 | 1,12-dodecamethylene diamine | 9.6 | 0.3 | 93–96 | 32–56 |
| 4 | 2-methyl-pentamethylene-1,5-diamine | 10.5 | 0 | 106–108 | 35–47 |
| 5 | 2,2,4(2,4,4)-trimethyl-hexamethylene 1,6-diamine (TMD) | 10.0 | 0 | 107–109 | 30–44 |
| 6 | 1,4-diaminocyclohexane | 10.3 | 0.3 | 120–130 | 53–85 |
| 7 | 4,4'-diamino-dicyclohexyl-methane - solid | 9.9 | 0.25 | 148–150 | 39–58 |
| 8 | 4,4'-diamino-dicyclohexyl-methane - liquid | 10.0 | 0.3 | 146–149 | 40–57 |
| 9 | 3,3'-dimethyl-4,4'-diamino-dicyclohexylmethane | 9.3 | 0 | 149–155 | 37–85 |
| 10 | N-cyclohexyl-propylene 1,3-diamine | 10.8 | 0.3 | 142–145 | 43–80 |
| 11 | bis-(1,4-aminomethyl)-cyclohexane | 10.9 | 0.5 | 133–140 | 50–80 |
| 12 | isophorone diamine (IPD) | 10.5 | 0.1 | 160–165 | 60–87 |
| 13 | 90 parts by weight IPD 10 parts by weight TMD | 9.9 | 0 | 146–157 | 49–72 |
| 14 | 70 parts by weight IPD 30 parts by weight TMD | 9.9 | 0 | 138–148 | 38–61 |
| 15 | 50 parts by weight IPD 50 parts by weight TMD | 10.2 | 0.1 | 125–127 | 34–58 |
| 16 | diethylene triamine | 11.1 | 0.4 | 162–165 | 45–88 |
| 17 | triethylene tetramine | 11.5 | 0.5 | 140–145 | 40–80 |
| 18 | tetraethylene pentamine | 12.0 | 0.3 | 120–123 | 40–75 |
| 19 | pentamethylene hexamine | 12.1 | 0.4 | 113–115 | 36–70 |
| 20 | dipropylene triamine | 11.8 | 0.4 | 153–155 | 40–65 |
| 21 | bis-(3-aminopropyl)-ethylene diamine | 11.6 | 0.5 | 152–155 | 42–68 |
| 22 | 3,5-diethyl-toluylene-diamine | 10 | 0 | 203–205 | 70–80 |
| 23 | 1,4-diamino-2,3,5,6-tetramethyl benzene | 10 | 0 | 175–177 | 55–72 |
| 24 | 4,4'-diaminodiphenyl-methane | 10 | 0.3 | 178–182 | 58–74 |
| 25 | 1,1,6,6-tetraisopropyl-2,5-diazahexane | 9.7 | 0.45 | 120–122 | 47–65 |
| 26 | N,N'-diisobutyl-isophorone-diamine | 9.4 | 0.3 | 130–132 | 45–65 |
| 27 | 4-(3-aminopropyl-amino)-2,2,6,6-tetramethylpiperidine | 10.1 | 0.5 | 125–129 | 35–49 |
| 28 | 4-[(bis-3-aminopropyl)-amino]-2,2,6,6-tetramethylpiperidine | 9.6 | 0.5 | 138–140 | 40–53 |
| 29 | melamine | 10.3 | 0.5 | 197–200 | 75–90 |
| 30 | N-(3-aminopropyl)glucamine | 9.5 | 0 | 124–126 | 33–95 |
| Example B b | | | | | |
| 1 | 4,4'-diamino-dicyclohexyl-methane - liquid | 10.2 | 0.1 | 144–147 | 41–59 |
| 2 | bis-(1,4-aminomethyl)cyclo-hexane | 10.8 | 0.3 | 136–141 | 53–75 |
| Example B c | | | | | |
| 1 | 4,4'-diaminodicyclohexyl-methane - liquid | 10.7 | 0 | 124–126 | 26–52 |
| Example B d | | | | | |

-continued

| | amine component | NCO content (% by weight) latent | Free | melting range °C. | glass transition temperature (DTA) °C. |
|---|---|---|---|---|---|
| 1 | 4,4'-diaminodicyclohexyl-methane - liquid | 10.6 | 0.1 | 105–111 | 24–52 |

Example B e

According to the general preparation B, the partially blocked IPDI adducts according to A 3, A 4 and A 5 underwent a reaction with 4,4'-diaminodicyclohexylmethane. The following table shows the chemical and physical characteristics of the product:

| Example B e | IPDI adduct according to | NCO content % by weight latent | free | melting range °C. | glass transition temperature (DTA) °C. |
|---|---|---|---|---|---|
| 1 | A 3 | 10.3 | 0.3 | 148–150 | 38–72 |
| 2 | A 4 | 10.2 | 0.1 | 155–161 | 37–78 |
| 3 | A 5 | 10.25 | 0.2 | 155–157 | 40–96 |

Example B f

According to the general preparation B, the partially blocked IPDI adducts according to A 2, were reacted with 4,4'-diaminodicyclohexylamethane, not in equivalent proportions, but rather in such proportions as to give a ratio of NCO to amine of X:1. The following table shows the chemical and physical characteristics for the product:

| Example B f | X | NCO content % by weight latent | free | melting range °C. | glass transition temperature (DTA) °C. |
|---|---|---|---|---|---|
| 1 | 1.05 | 9.9 | 0.4 | 145–148 | 35–58 |
| 2 | 1.1 | 10.7 | 0.8 | 140–142 | 33–59 |
| 3 | 1.2 | 11.5 | 1.4 | 138–140 | 35–58 |
| 4 | 1.3 | 12.0 | 1.95 | 131–136 | 33–55 |

Example B g

According to the general preparation for the blocked polyisocyanate-urea-adducts, at X °C., the partially blocked IPDI adducts according to Example A 2, underwent a reaction with 4,4'-diaminodicyclohexylmethane and in the following table the chemical and physical characteristics of the inventive and comparative reaction products are shown.

| Example B g | | Reaction Temperature X °C. | NCO content % by weight latent | free | glass transition temperature in °C. (DTA) |
|---|---|---|---|---|---|
| 1 | | 40 | 10.27 | 0.2 | 36–59 |
| 2 | | 50 | 10.25 | 0.3 | 38–58 |
| 3 | I | 60 | 10.1 | 0.2 | 40–57 |
| 4 | | 70 | 10.3 | 0.25 | 40–59 |
| 5 | | 80 | 10.0 | 0.15 | 40–56 |
| 6 | | 90 | 10.3 | 0.1 | 28–81 |
| 7 | II | 100 | 10.2 | 0 | 19–90 |
| 8 | | 110 | 10.15 | 0.2 | 17–125 |

Remarks:
I = invention
II = comparison

Example B h1

With respect to the free NCO content, 210 parts by weight of 4,4'-diamino- dicyclohexylmethane were added to 730 parts by weight of a partially blocked IPDI of a A 2, dissolved in 506 parts by weight of acetone with intensive stirring, at a temperature ranging from 55° to 65° C. in such a manner that the reaction temperature does not exceed 65° C. Following completion of diamine addition, the reaction mixture was then stirred for a period ranging from 30 to 45 minutes urea NCO content has dropped to 0.5% by weight. Then the acetone was removed from reaction product under a vacuum at 0.133 mbar. The reaction product had the following chemical and physical characteristics:
NCO content (latent): 10.3% by weight
NCO content (free): 0.3% by weight
melting range glass transition: 147°–149° C.
temperature (DTA) 40°–59° C.

Example B h2

According to Example B h1, the reaction was carried out in acetic ester. The reaction product had the following chemical and physical characteristics:
NCO content (latent): 10.4% by weight
NCO content (free): 0% by weight
melting range glass transition: 146°–148° C.
temperature (DTA) 46°–59° C.

EXAMPLE B i

With respect to the free NCO content, Z parts by weight of water were added to X parts by weight of a partially blocked IPDI of A 2 and 0.15% by weight of DBTL, with respect to the partially blocked IPDI added, dissolved in Y parts by weight of acetone with intensive stirring, at a temperature ranging from 50° to 60° C. in such a manner that the reaction temperature does not exceed 65° C. Following completion of water addition, the reaction mixture was then heated with stirring until the calculated $CO_2$ quantity had been evolved. Then the reaction was analyzed by volumetric analysis of NCO by titration and the acetone was removed from the reaction product under a vacuum at 0.133 mbar. The quantities and the corresponding chemical and physical characteristics were compiled in the following table:

| Example | in % by wt. | | | | NCO content range | | melting DTA* | |
|---|---|---|---|---|---|---|---|---|
| B i | X | Y | Z | $CO_2$ (l) | total | free | °C. | °C. |
| 1 | 359 | 146 | 9 | 11.3–12 | 12.5 | 0.3 | 105–107 | 45–65 |
| 2 | 185 | 120 | 3.45 | 4.3–4.6 | 15.2 | 2.1 | 94–96 | 38–56 |

*glass transition temperature

Example B j

With respect to the free NCO content, the calculated quantity of amine component was added dropwise to 730 parts by weight of a partially blocked IPDI of A 2, dissolved in from 500 to 550 parts by weight of special benzene (contains 3% by vol. of aromatics) or cyclohexane with intensive stirring, at room temperature in such a manner that the reaction temperature does not exceed 70° C. During the addition of diamine the polyisocyanate-urea-adduct precipitated out. Following completion of the diamine addition, the reaction mixture was then stirred for a period ranging from 30 to 45 minutes and then following volumetric analysis of NCO by titration, freed of the solvent. The following table gives the chemical and physical characteristics of the product:

| Example B j | amine component | NCO content % by weight | | melting range °C. | glass transition temperature (DTA) °C. |
|---|---|---|---|---|---|
| | | total | free | | |
| Ratio of NCO to amine = 1:1 | | | | | |
| 1 | 4-4'-diaminodi-cyclohexylmethane-liquid | 9.5 | 0.4 | 146–149 | 36–63 |
| 2 | bis-(1,4-aminomethyl-cyclohexane | 10.2 | 0.4 | 134–136 | 45–95 |
| 3 | isophorone diamine | 10.0 | 0.4 | 154–159 | 56–84 |
| 4 | pentaethylene-hexane | 11.3 | 0 | 123–127 | 37–65 |
| Ratio of NCO to amine 1.1:1.2:1.3:1 | | | | | |
| 5 | 4,4'-diaminodi-cyclohexylmethane | 10.9 | 0.8 | 137–141 | 37–60 |
| 6 | 4,4'-diaminodi-cyclohexylmethane | 11.2 | 1.5 | 140–141 | 33–59 |
| 7 | 4,4'-diaminodi-cyclohexylmethane | 12.1 | 1.9 | 133–135 | 32–56 |

C. Preparation of blocked polyisocyanate-urea-adducts according to the invention in conventional paint solvents With respect to the free NCO content, the equivalent quantities (dissolved or neat) of a diamine or polyamine or their mixtures were added to a from 30 to 50% conventional paint solvent solution of a partially blocked polyisocyanate with intensive stirring, at a temperature ranging from 50° to 60° C. in such a manner that the reaction temperature does not exceed 70° C. Following completion of amine addition, the reaction mixture was then heated urea NCO content has dropped to zero. The following table lists the chemical and physical characteristics of the product:

| Example C a | amine component | concentration of urea adduct | solvent | | | NCO content (latent) % by weight | Viscosity DIN-4-cup 20° C. (sec) | mPa's 25° C. |
|---|---|---|---|---|---|---|---|---|
| 1 | 2,2,4(2,4,4)-trimethyl-hexamethylene-1,6-diamine (TMD) | 40 | S* | 100 | | 4.2 | 116 | 330 |
| | | 50 | E*/S | 100 | 1:2 | 5.3 | 345 | 1,040 |
| 2 | pentaethylene-hexamine (PEHA) | 40 | S | 100 | | 4.6 | 32 | 90 |
| | | 50 | E/S | 100 | 1:2 | 5.8 | 200 | 644 |
| 3 | bis-(1,4-aminomethyl)-cyclohexane (HXDA) | 40 | E/S | 100 | 1:2 | 4.3 | — | 7,000 |
| 4 | isophorone diamine | 30 | E/S | 100 | 1:2 | 3.1 | 151 | 410 |
| | | 40 | E/S | 100 | 1:2 | 4.1 | — | 15,600 |
| 5 | HXDA/PEHA 2:1 | 30 | E/S | 100 | 1:2 | 3.4 | 190 | 489 |
| | | 40 | E/S | 100 | 1:2 | 4.2 | 190 | 490 |
| 6 | IPD/PEHA 2:1 | 40 | E/S | 100 | 1:2 | 4.2 | 166 | 472 |
| 7 | HXDA/TMD 1:1 | 30 | E/S | 100 | 1:2 | 3.1 | 72 | 177 |
| | | 40 | E/S | 100 | 1:2 | 4.1 | 754 | 2,086 |

S* = SOLVESSO ®,
E* = EGA

Example C b

With respect to the free NCO content, Z parts by weight of water were added to X parts by weight of a partially blocked IPDI of example A 1 and 0.15% by weight of DBTL, with respect to the partially blocked IPDI added, dissolved in Y parts by weight of conventional paint solvent with intensive stirring, at a temperature ranging from 55° to 60° C. in such a manner that the reaction temperature does not exceed 65° C. Following completion of water addition, the reaction mixture was then heated with stirring urea calculated $CO_2$ quantity has been evolved. The reaction was then analyzed via volumetric analysis of NCO by titration. The quantities and the corresponding chemical and physical characteristics were listed in the following table:

| Example C b | $CO_2$ X | Y | Z | NCO content in % by wt. (I) total | free | outflow in DIN-4-cup 20° C. in sec | time of |
|---|---|---|---|---|---|---|---|
| 1 | 185 | 120 | 3.45 | 4.2–4.6 | 9.4 | 1.6 | 215 |
| 2 | 183.3 | 120 | 2.3 | 2.8–3.0 | 10.9 | 3.4 | 50 |
| 3 | 181.6 | 120 | 1.15 | 4.2–4.5 | 12.8 | 5.0 | 20 |

D. I. Comparison examples - General preparation (partially blocked polyisocyanates without thin-layer evaporation)

One mole of blocking agent was added in such a manner to one mole of polyisocyanate at a temperature ranging from 90° to 110° that the temperature of the reaction mixture does not exceed 120° C. After completion of the addition of blocking agent, the reaction mixture was heated urea NCO content of the reaction mixture has reached the calculated value. The following table shows the chemical and physical characteristics of the reaction products:

| Example DI | polyisocyanate | blocking agent | NCO content % by weight free | total | Polyisocyanate monomer % by wt. | Viscosity in mPa's at °C. 25 | 30 | 40 | 50 | 70 |
|---|---|---|---|---|---|---|---|---|---|---|
| 1 | IPDI | caprolactam | 12.4 | 24.85 | 15.8 | 381,000 | 142,000 | 27,800 | 6,650 | 690 |
| 2 | IPDI | MEK-oxime | 12.4 | 26.0 | 15.3 | 27,000 | 14,750 | 3,390 | 1,100 | 195 |
| 3 | HDI | caprolactam | 14.7 | 29.75 | 14.5 | 90 | 70 | 60 | 40 | <30 |
| 4 | HDI | MEK-oxime | 16.4 | 31.5 | 14.5 | 75 | 55 | 35 | 30 | <30 |
| 5 | DI51 | caprolactam | 14.5 | 29.0 | 14.3 | 190 | 140 | 70 | 40 | <30 |
| 6 | DI51 | MEK-oxime | 16.2 | 31.7 | 17.7 | 110 | 85 | 45 | 30 | <30 |
| 7 | HMDI | caprolactam | 10.9 | 21.9 | 17.0 | 880,000 | 300,000 | 60,000 | 9,000 | 1,100 |

D. II. Comparison examples (polyisocyanate-urea-adducts)

According to the general preparation B for the blocked polyisocyanate-urea-adducts, the partially blocked polyisocyanates of D I underwent a reaction with the amine component. The chemical and physical characteristics were compiled in the following table:

| Example D II | polyisocyanate | amine component | NCO content % by weight total | free | melting range °C. | glass transition (DTA) °C. |
|---|---|---|---|---|---|---|
| 1 | 1 | 4,4'-diamino-dicyclohexyl-methane | 9.4 | 0.2 | 158–160 | 19–110 |
| 2 | 3 | 4,4'-diamino-dicyclohexyl-methane | 10.6 | 0.1 | 102–104 | 17–38 |
| 3 | 5 | 4,4'-diamino-dicyclohexyl-methane | 10.8 | 0 | 90–92 | 14–34 |
| 4 | 7 | 4,4'-diamino-dicyclohexyl-methane | 8.5 | 0 | 160–162 | 26–85 |
| 5 | 1 | IPD | 9.9 | 0 | 141–145 | 20–83 |

In all of the examples more or less severe incompatibilities (agglomeration) occurred as early as during the amine addition so that the course of the reaction between NCO and amino groups was not without problems. The polyisocyanate-urea-adducts still exhibit weak basicity.

D. III Comparison examples (Polyisocyanate-urea-adducts in conventional paint solvents)

If according to the general preparation C, the partially blocked polyisocyanates of D I undergo reaction with the amine component, the polyisocyanate-urea-adducts precipitate out already during the amine addition and cannot be used for manufacturing solvent-containing paint systems.

Obviously, numerous modifications and variations of the present invention are possible in light of the above teachings. Accordingly, the invention may be practiced otherwise than as specifically described herein.

What is claimed as new and desired to be secured by Letters Patent of the United States is:

1. A process for the production of a blocked urea group-containing polyisocyanate from a partially blocked polyisocyanate and a polyamine, comprising the steps of:

(i) reacting a partially blocked polyisocyanate, said polyisocyanate being made substantially free of monomeric polyisocyanate, by vacuum thin layer evaporation, with a primary polyamine, secondary polyamine, or mixtures thereof, in relative proportions such that the ratio of isocyanate groups to amino groups is in the range from about 1:1 to 1.3:1, and (ii) isolating said urea group-containing polyisocyanate by wherein the vacuum boiling point of said polyisocyanate is lower than the deblocking temperature of said urea group-containing polyisocyanate.

2. The process of claim 1, wherein said partially blocked polyisocyanate is prepared by adding 1 mole of blocking agent to from 5–20 moles of polyisocyanate.

3. The process of claim 1, wherein said isolated urea group-containing polyisocyanate has a monomeric, unblocked polyisocyanate content of 6.5 wt. % or less.

4. The process of claim 3, wherein said isolated urea group-containing polyisocyanate has a monomeric unblocked polyisocyanate content of 3.5 wt. % or less.

5. The process of claim 4, wherein the isolated urea group-containing polyisocyanate has a monomeric unblocked polyisocyanate content of 2.5 wt. % or less.

6. The process of claim 1, wherein said polyamine is selected from the group consisting of polyamines having formula I and II shown below:

$$\begin{matrix} H & & & H \\ & N-R-N & & \\ H & & & H \end{matrix} \quad (I)$$

in which R is —(CH$_2$)—$_{2-36}$, or C$_{2-36}$ branched alkyl,

[structures shown]

-continued

[structure shown]

and $$\begin{matrix} R^1 & & & & & H \\ & N-(R^2)_m-NH-(R^2)_n-\!\!\!\!\!\!\!\!\!\!\!\!\!\!\!\overline{\phantom{x}}\!\!\!\!\!\!\!\!\!-N & \\ H & & & & & R^3 \end{matrix} \quad (II)$$

wherein R$^1$ and R$^3$ are, independently, hydrogen or a straight chain or branched alkyl, cycloakyl, aryl or aralkyl, R$^2$ is —CH$_2$— a branched alkyl group, m=2-8, X=0-6, n=2-8 and said polyamine contains 2-36 carbon atoms.

7. The process of claim 6, wherein said polyamine is selected from the group consisting of 1,12-dodecamethylene diamine, 3,3'-dimethyl-4,4'-diaminodicyclohexylmethane, tetraethylene pentamine, pentaethylene hexamine and 4,4'-diaminophenylmethane.

8. The process of claim 6, wherein said polyamine is selected from the group consisting of 4,4'-diaminodicyclohexylmethane, bis-(1,4-aminomethyl)cyclohexane, isophorone diamine, 2,2,4(2,4,4)-trimethylhexamethylene-1,6-diamine and mixtures thereof.

9. The process of claim 1, wherein said polyisocyanate is an aliphatic or cycloaliphatic diisocyanate and mixtures thereof.

10. The process of claim 9, wherein said diisocyanate is selected from the group consisting of 1,6-hexamethylene-diisocyanate, 2-methylpentane-1,5-diisocyanate, 2,2,4(2,4,4)-trimethylhexamethylene-1,6-diisocyanate and mixtures thereof.

11. The process of claim 9, wherein said diisocyanate is 3-isocyanatomethyl-3,5,5-trimethylcyclohexylisocyanate.

12. The process of claim 1, wherein said partially blocked polyisocyanate, said polyamine or both are used in said reacting step as solvent solutions.

13. The process of claim 12, wherein said polyamine is added neat or in a solvent.

14. The process of claim 12, wherein said solvent is a conventional paint solvent.

15. The process of claim 12, wherein said solvent is selected from the group consisting of toluene, cyclohexane and special benzene, said special benzene containing less than 1% by volume of aromatics.

16. The process of claim 1, wherein said reacting step is conducted at a temperature ranging from ambient temperature to 80° C.

17. The process of claim 16, wherein said reacting step is conducted at a temperature between ambient temperature and 70° C.

18. The process of claim 1, wherein said blocked urea group-containing polyisocyanate has a NCO content ranging from about 4 to 20 wt. %.

19. The process of claim 1, wherein said blocked urea group-containing polyisocyanate has a NCO content ranging from about 6 to 15 wt. %.

20. The process of claim 1, wherein said blocked urea group-containing polyisocyanate has a NCO content of 5% by weight or less.

* * * * *